US009170198B2

(12) United States Patent
Estrada

(10) Patent No.: US 9,170,198 B2
(45) Date of Patent: Oct. 27, 2015

(54) CROSSTALK REDUCTION

(71) Applicant: Luminex Corporation, Austin, TX (US)

(72) Inventor: Arnold Estrada, Austin, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 14/573,950

(22) Filed: Dec. 17, 2014

(65) Prior Publication Data

US 2015/0177148 A1 Jun. 25, 2015

Related U.S. Application Data

(60) Provisional application No. 61/962,302, filed on Dec. 19, 2013.

(51) Int. Cl.
*G01N 21/64* (2006.01)

(52) U.S. Cl.
CPC ........ *G01N 21/6428* (2013.01); *G01N 21/6486* (2013.01); *G01N 2201/121* (2013.01)

(58) Field of Classification Search
CPC ............... G01N 21/6439; G01N 2021/6446; G01N 2021/6421; G01N 21/6408
USPC ...................................................... 250/459.1
See application file for complete search history.

(56) References Cited

U.S. PATENT DOCUMENTS

| 7,839,507 B2 | 11/2010 | Gunstream et al. |
| 2002/0098588 A1* | 7/2002 | Sammak et al. ................ 436/8 |
| 2004/0121483 A1* | 6/2004 | Corson et al. ................ 436/172 |
| 2006/0269922 A1* | 11/2006 | Sagner et al. .................... 435/6 |
| 2010/0015611 A1 | 1/2010 | Webster et al. |
| 2012/0171677 A1* | 7/2012 | Ludowise .................... 435/6.11 |

FOREIGN PATENT DOCUMENTS

| WO | 03012437 | 2/2003 |
| WO | 2011031585 | 3/2011 |

OTHER PUBLICATIONS

International Search Report and Written Opinion in Application No. PCT/US2014/071201 mailed Mar. 6, 2015, 10 pages.
Eric B. Shain and John M. Clemens, "A new method for robust quantitative and qualitative analysis of real-time PCR," Nucleic Acids Research, vol. 36, No. 14 e91, published online Jul. 4, 2008, 7 pages.
George V. Dimitrov, et al., "Simulation analysis of the ability of different types of multielectrodes to increase selectivity of detection and to reduce crosstalk," Journal of Electromyography and Kinesiology 13, 2003, pp. 125-138.

* cited by examiner

*Primary Examiner* — Kiho Kim
(74) *Attorney, Agent, or Firm* — Meyertons, Hood, Kivlin, Kowert & Goetzel, P.C.

(57) ABSTRACT

Techniques are disclosed relating to analysis and reduction of crosstalk between signals. These techniques may be applicable in many fields, such as single-tube PCR or DNA melt analysis, PCR or melt data from neighboring wells of a multi-well plate, capillary electrophoresis data (e.g., DNA sequencing), gas chromatography, multispectral imaging, dual-color fluorescence correlation spectrometry, electrical crosstalk, etc. According to one embodiment, crosstalk between fluorescence signals from different species may be determined based on a correlation between the time derivatives of the fluorescence signals from the fluorescent species.

23 Claims, 8 Drawing Sheets

CROSSTALK REDUCTION

CROSS-REFERENCE TO RELATED APPLICATIONS

This application claims the benefit of U.S. Prov. App. No. 61/962,302, filed on Dec. 19, 2013. (U.S. Prov. App. No. 61/962,302 was originally filed as a non-provisional application with U.S. application Ser. No. 14/135,106, and it was then converted to a provisional application.)

BACKGROUND

1. Technical Field

This disclosure relates to analysis and correction of crosstalk between signals. In particular, this disclosure relates to a technique for more accurately determining the amount of crosstalk between signals, which may be useful in determining the levels of the underlying signals.

2. Description of the Related Art

It is a well-known problem in many different technical fields that measured signals may sometimes exhibit crosstalk. Crosstalk can, for example lead to erroneous changes in the data from one channel as a result of changes in a neighboring channel, which may impede the ability to determine the levels of the underlying signals in each channel. Accordingly, determining the amount of crosstalk and how to accurately correct for it is an important issue in many different areas. This disclosure includes techniques of general applicability that may be applied in different situations according to various embodiments.

For example, this disclosure includes techniques that may be applicable in such varied fields as single-tube polymerase chain reaction (PCR) or DNA melt analysis, PCR or melt data from neighboring wells of a multi-well plate or other multi-well arrangement, capillary electrophoresis data (e.g., DNA sequencing), gas chromatography, multispectral imaging, dual-color fluorescence correlation spectrometry, electrical crosstalk, etc.

In one embodiment, this disclosure may be applied to quantitative polymerase chain reaction (qPCR) devices used to amplify nucleic acid sequences. Some such devices may typically have multiple spectral channels to allow for multiplexed reactions. A problem sometimes encountered is that spectral overlap of the absorption and emission spectra of the fluorescent species (e.g., fluorophores) used to measure the real-time products of the reaction leads to crosstalk between the spectral channels. The signature of crosstalk in qPCR data is that a change in one channel's data can be seen in another channel's data. Crosstalk can reduce the effective limit of detection of an assay or lead to inconsistent or incorrect assay results.

According to one known technique, and as discussed in more detail below, crosstalk may be estimated statically based on determined characteristics of the measuring device. Such a method may have various drawbacks, however. The levels of crosstalk may in fact not be completely static, which can cause inaccuracies in the static estimate as the crosstalk varies. Accordingly, this disclosure provides various methods for determining crosstalk dynamically, based on analysis of the captured data.

SUMMARY

According to one embodiment, this disclosure provides for a method including illuminating a sample with a light source. According to this method, the sample includes a plurality of fluorescent species, and illuminating the sample excites at least two of the fluorescent species. This method further includes measuring a fluorescence signal from the sample, including component signals from the at least two fluorescent species. Finally this method includes determining, by an assaying device, an amount of crosstalk between at least two component signals included in the fluorescence signal based on a correlation between respective time derivatives of the at least two component signals.

According to a second embodiment, this disclosure provides for an apparatus including a light source configured to illuminate a sample having first and second fluorescent species. The apparatus further includes a detector configured to receive fluorescent light from the sample in response to the illumination. Finally, the apparatus includes a processing unit configured to receive data indicative of the received fluorescent light. The processing unit is further configured to determine an amount of crosstalk between the data based on a correlation between respective time derivatives of the first and second data.

According to a third embodiment, this disclosure provides for a non-transitory computer-readable medium having instructions coded thereon that, when executed by a computing device, cause the computing device to carry out certain operations. The operations according to this embodiment include receiving data indicative of a plurality of time-varying signals, where the signals include crosstalk between at least first and second ones. The operations further include determining respective time derivatives for the signals based on the data, determining an amount of correlation between the respective time derivatives, and determining a crosstalk metric indicative of a level of crosstalk for the signals, wherein the crosstalk metric is based on the amount of correlation. The operations finally include iteratively adjusting a plurality of crosstalk coefficients indicative of the crosstalk between the signals based on the crosstalk metric.

TERMINOLOGY

The following paragraphs provide definitions and/or context for terms found in this disclosure (including the appended claims).

"Embodiment." This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

"Based On." As used herein, this term is used to describe one or more factors that affect a determination. This term does not foreclose additional factors that may affect a determination. That is, a determination may be solely based on those factors or based only in part on those factors. Consider the phrase "determine A based on B." This phrase connotes that B is a factor that affects the determination of A, but does not foreclose the determination of A from also being based on C. In other instances, A may be determined based solely on B.

"Configured To" or "Operable To." Various units, circuits, or other components may be described or claimed as "configured to" perform a task or tasks. In such contexts, the phrases "configured to" and "operable to" may be used to connote structure by indicating that the units/circuits/components include structure (e.g., circuitry) that performs the task or tasks during operation. As such, the unit/circuit/component can be said to be configured to perform the task even when the specified unit/circuit/component is not currently operational (e.g., is not on). The units/circuits/components used with the "configured to" language include hardware—for example, circuits, memory storing program instructions executable to implement the operation, etc. Reciting that a unit/circuit/component is "configured to" perform one or more tasks is expressly intended not to invoke 35 U.S.C. §112(f) for that unit/circuit/component.

It is to be understood the present disclosure is not limited to particular devices or methods, which may, of course, vary. It is also to be understood that the terminology used herein is for the purpose of describing particular embodiments only, and is not intended to be limiting. As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

DETAILED DESCRIPTION

Figure 1:
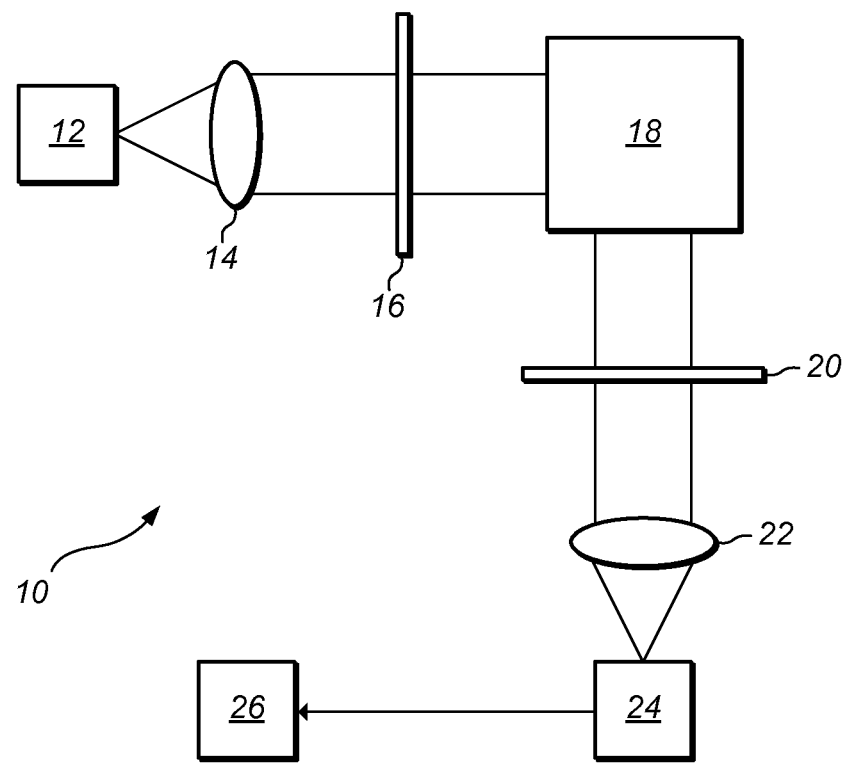
FIG. 1 shows a schematic of an embodiment of a PCR device.

Turning now to FIG. 1, a block diagram illustrating one embodiment of a PCR system 10 according to the present disclosure is shown. This disclosure is of course not limited to PCR devices, but FIG. 1 is provided to give context for one exemplary embodiment. In the illustrated embodiment, this system includes light source 12, input lens 14, input filter 16, PCR tube 18, output filter 20, output lens 22, detector 24, and analysis hardware 26.

Many embodiments of PCR devices are well-known in the art, and this disclosure may find applicability in any suitable system. For example, this disclosure may be used in conjunction with standard PCR systems, real-time PCR systems, single-tube PCR systems, multi-well PCR systems, quantitative PCR systems, other assaying systems and devices, etc.

It is to be noted that some aspects of this disclosure refer to PCR embodiments in which the fluorescence signal decreases with time (or with cycle number). This is due to the use of a quenching reaction in some embodiments. One of ordinary skill in the art will recognize the modifications that may be made in the case of a PCR reaction in which fluorescence increases with time instead of decreasing.

In PCR system 10, light source 12 provides illumination to excite various fluorescent species (e.g., fluorophores) within PCR tube 18. In various locations throughout this disclosure, the fluorophores FAM and HEX will be referred to; however, many fluorescent species are known in the art, and these two are provided only for illustrative purposes.

The illumination from light source 12 may be focused or collimated by input lens 14 and wavelength-filtered by input filter 16. In some embodiments, light source 12 may be a broad-spectrum source (e.g., white light), with wavelength selectivity provided by input filter 16. In other embodiments, however, light source 12 may itself be narrow-spectrum (e.g., an LED or laser light source). In these embodiments, it may be possible to omit input filter 16.

During the course of the reaction carried out in PCR tube 18, fluorescent light emitted by the various fluorescent species within PCR tube 18 may be captured by detector 24. In some embodiments, the fluorescent light may first be wavelength-filtered at output filter 20 and/or focused at output lens 22 before being detected at detector 24. Detector 24 may be any suitable light detector, such as a photo-detector, charge-coupled device (CCD) detector, photomultiplier tube, etc. Analysis hardware 26 then receives data from detector 24. Analysis hardware 26 may include any suitable computing device as known in the art, and may include one or more processors, memory, and/or non-transitory computer-readable media. The elements of PCR system 10 may be integrated into a single device, or they may be connected together from separate elements. Analysis hardware 26 may be used to carry out any of the methods disclosed herein.

Figure 2:
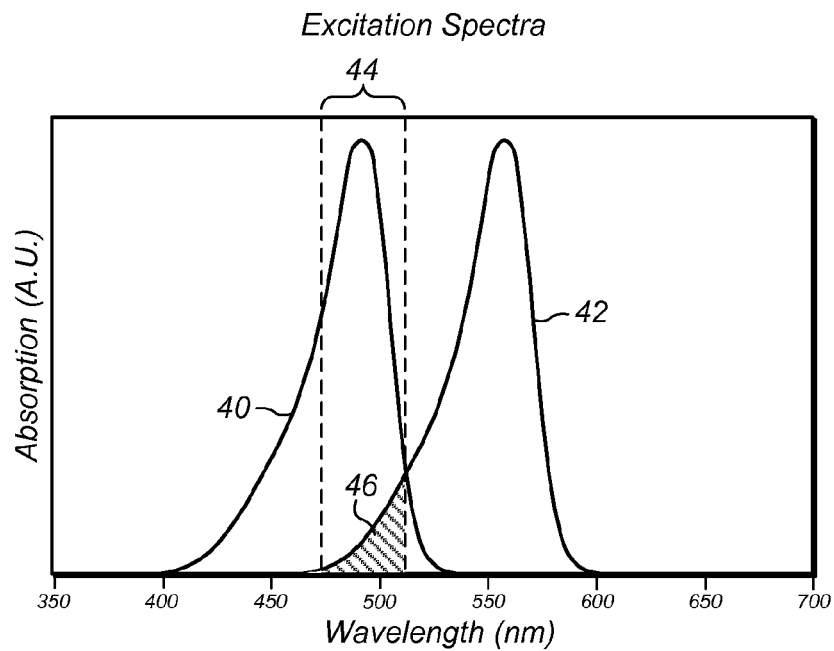
FIG. 2 shows excitation spectra for two fluorescent species.

Turning now to FIG. 2, a graph illustrating exemplary excitation spectra 40 and 42 for two fluorescent species is shown. Absorption in arbitrary units (A.U.) is shown on the vertical axis, and wavelength in nanometers (nm) is shown on the horizontal axis. Throughout this disclosure, various graphs of exemplary spectra are shown. In some illustrations (including FIG. 2), spectral curves for different species will be shown as having essentially the same shape for simplicity. One of ordinary skill in the art will understand, however, that in typical real-world spectra, the shape of such curves may typically be somewhat different.

When testing for the presence of the first species (i.e., the species with excitation spectrum 40), an optical filter 44 such as input filter 16 from FIG. 1 may be used to limit the wavelength of the incident light to a region near the absorption peak of the first species. In other embodiments, a narrow-spectrum light source may be used to achieve the same effect. The purpose of this is to attempt to excite the first species approximately in isolation; however, because absorption spectra 40 and 42 overlap, some degree of excitation of the second species may be unavoidable in some cases. Overlap region 46 illustrates the region of cross-excitation that occurs with optical filter 44.

Figure 3:
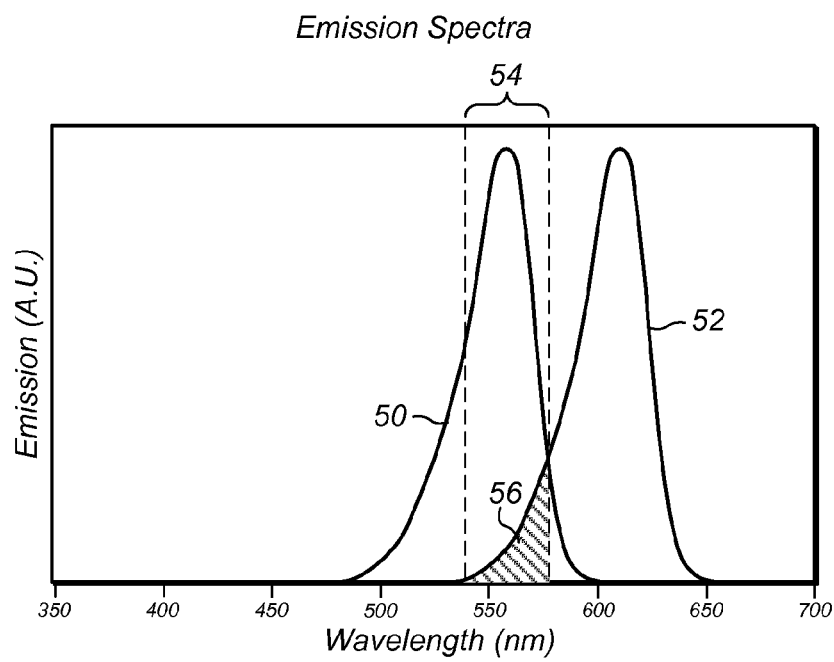
FIG. 3 shows emission spectra for the fluorescent species of FIG. 2.

Turning now to FIG. 3, a similar graph is provided, but with the emission spectra of the two species shown instead of the excitation spectra. As is typical in fluorescence spectra, emission spectra 50 and 52 of the first and second species are shown as having longer wavelengths than their corresponding absorption spectra from FIG. 2.

Emission spectra 50 and 52 are also shown as partially overlapping, similarly to absorption spectra 40 and 42. Again, this can be mitigated somewhat through the use of optical filter 54 (e.g., output filter 20 from FIG. 1). However, even with the use of optical filter 54, some degree of crosstalk between the emission spectra may be unavoidable. Overlap region 56 illustrates the region of cross-emission that occurs with optical filter 54.

Accordingly, it may become difficult when performing measurements on these samples to determine how much of a measured signal is attributable to each species. In the case of only two species, it may be possible to select species that have absorption and/or emission spectra that do not substantially overlap. In this way, the problem of crosstalk may be substantially mitigated or even eliminated in systems that use only two fluorescent species. However, the teachings of this disclosure may still be applicable even in a system with only two fluorescent species, due to the fact that some overlap may still occur in some embodiments.

Figure 4:
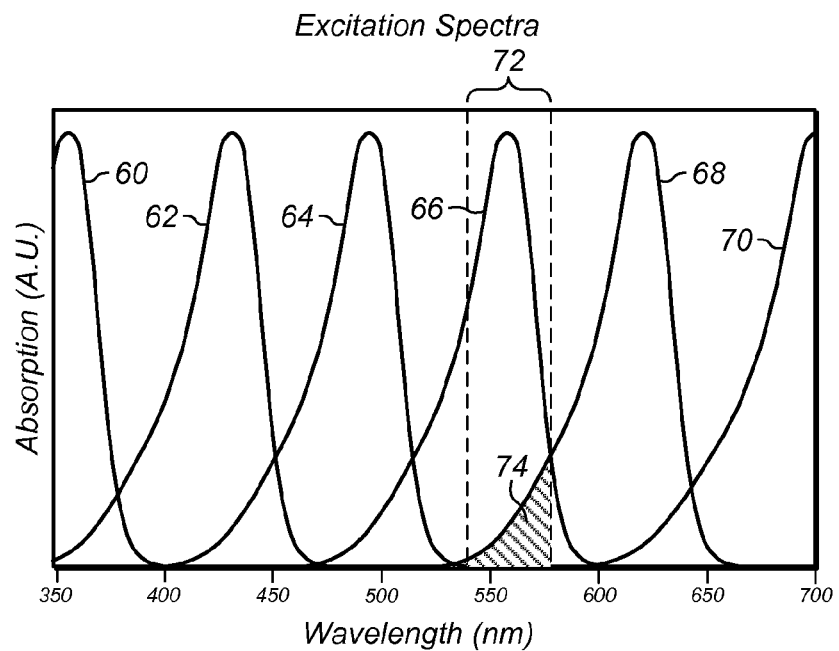
FIG. 4 shows excitation spectra for six fluorescent species.
Figure 5:
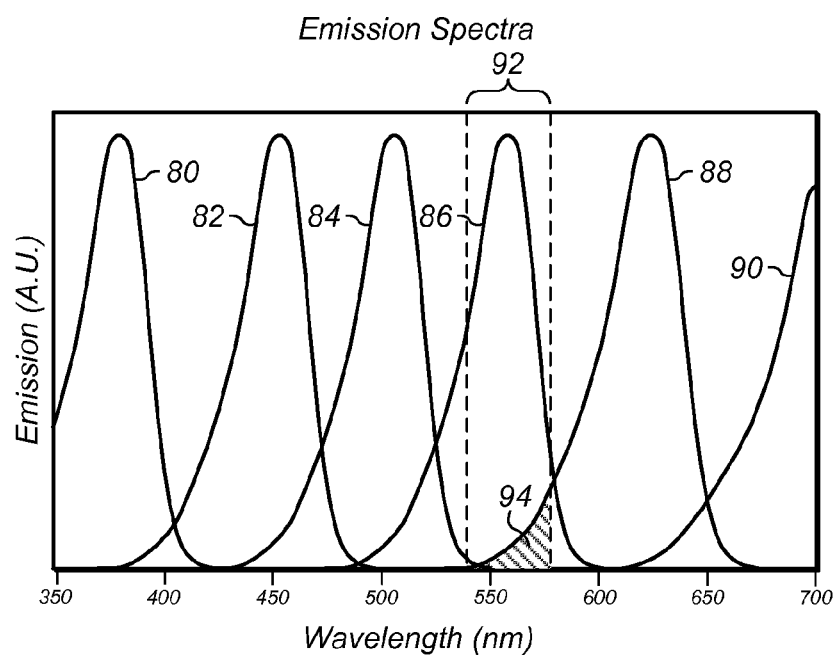
FIG. 5 shows emission spectra for the fluorescent species of FIG. 4.

Turning now to FIGS. 4 and 5, excitation and emission spectra similar to those of FIGS. 2 and 3 are shown. In FIGS. 4 and 5, however, six separate fluorescent species are present in the sample, and several regions of cross-excitation and cross-emission are shown (some of which involve more than two of the species). In FIG. 4, excitation spectra 60, 62, 64, 66, 68, and 70 are shown for the six species in the sample. Optical filter 72 is used in this embodiment to attempt to isolate excitation spectrum 66, but there is some amount of overlap shown at overlap region 74.

Correspondingly, in FIG. 5, emission spectra 80, 82, 84, 86, 88, and 90 are shown for the six species in the sample. Optical filter 92 is used in this embodiment to attempt to isolate emission spectrum 86, but there is some amount of overlap shown at overlap region 94.

As noted above, in embodiments with only two species it may be possible to simply select species having spectra that do not appreciably overlap. Such a solution may not be possible, however, in an embodiment with six species as shown in FIGS. 4 and 5. Due to the breadth of the peaks in the excitation and emission spectra, as well as the available range of fluorescent wavelengths, it may be that some unavoidable amount of crosstalk exists in such an embodiment. In some embodiments, crosstalk may be limited to adjacent spectra (e.g., the overlap regions include signals from only two spectra); in other embodiments, however, there may be overlap from three or even more spectra.

According to other embodiments, even more than six fluorescent species may be present in a sample. As the number of fluorescent species increases, the crosstalk effect may become more pronounced and more unavoidable. Accordingly, the techniques of this disclosure may have particular applicability in systems with a relatively large number of channels (e.g., 4, 5, 6, 7, 8, 9, 10, or even more channels).

For the sake of simplicity, some of the following discussion will refer to systems having only two fluorescent species and make the assumption that there is some degree of crosstalk. One of ordinary skill in the art will understand how such discussion generalizes to embodiments with more than two fluorescent species.

According to one known method for reducing crosstalk, it may be observed that each fluorescence measurement is a linear combination of signals from multiple fluorescent species. This method involves characterizing the signature of each fluorescent species at a particular concentration across all of the spectral channels. The result is a "crosstalk matrix" where each column indicates the amount of signal detected in each spectral channel from a fluorophore. The crosstalk matrix may be measured during calibration of the device.

For example, consider an embodiment that uses FAM and HEX as its two fluorescent species. In this embodiment, the relationship between the fluorescence measurements and the actual signals is as follows:

$$F_{FAM} = M_{1,1} C_{FAM} + M_{1,2} C_{HEX} \quad (1)$$

$$F_{HEX} = M_{2,1} C_{FAM} + M_{2,2} C_{HEX} \quad (2)$$

In these equations, the F's denote the measured fluorescence signals, and the C's denote the intensities of the underlying emissions from the respective fluorescent species (which may typically be considered to be proportional to the concentrations of the underlying fluorescent species). The M's are crosstalk coefficients that describe the relative amounts of crosstalk and may be determined based on various testing protocols used to characterize the operation of the device (e.g., the assaying device). In some embodiments, a matrix formulation may be convenient. Equations (1) and (2) may be written in matrix form as:

$$\begin{bmatrix} F_{FAM} \\ F_{HEX} \end{bmatrix} = \begin{pmatrix} M_{1,1} & M_{1,2} \\ M_{2,1} & M_{2,2} \end{pmatrix} \begin{bmatrix} C_{FAM} \\ C_{HEX} \end{bmatrix} \quad (3)$$

Figure 7A:
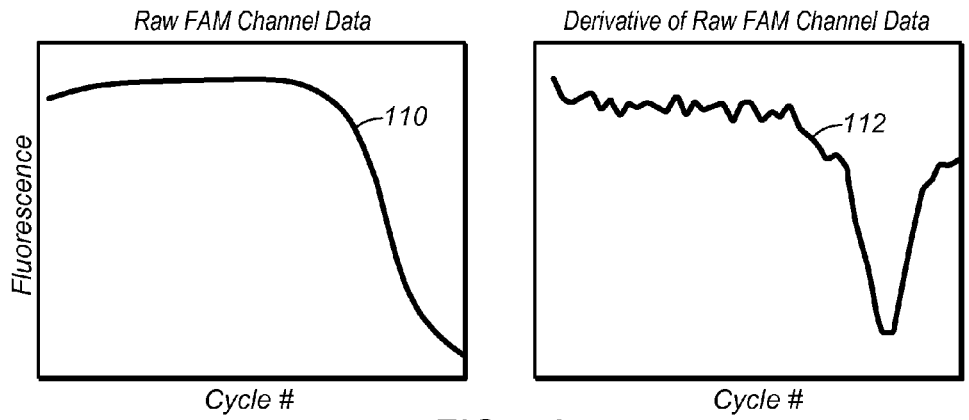
FIGS. 7A and 7B show raw data for two PCR channels.

$F_{FAM}$ and $F_{HEX}$ are vectors representing a series of measurements at varying cycle number and/or temperatures. Equation (3) applies for each measurement in the vector. In FIG. 7A, line 110 represents the $F_{FAM}$ vector and in FIG. 7B line 114 represents the $F_{HEX}$ vector.

Because what is typically desired is the C quantities, Equation (3) may be rearranged into a more useful form as follows to isolate the signals proportional to the concentrations of the respective fluorescent species.

$$\begin{bmatrix} C_{FAM} \\ C_{HEX} \end{bmatrix} = \begin{pmatrix} M_{1,1} & M_{1,2} \\ M_{2,1} & M_{2,2} \end{pmatrix}^{-1} \begin{bmatrix} F_{FAM} \\ F_{HEX} \end{bmatrix} \quad (4)$$

Accordingly, a crosstalk matrix may be determined based on device characteristics and then used to correct for crosstalk and isolate the signals from individual fluorescent species. Typically, the device may be characterized once at the time of manufacture to determine the coefficients of the crosstalk matrix. The coefficients being used typically do not change (unless the device is later recalibrated). Thus the coefficients are generally taken as static across different runs of data. Accordingly, this method will be referred to herein as the "static crosstalk matrix" method.

As one example, the following is an exemplary static crosstalk matrix (normalized to each channel's total signal) for a two-plex system utilizing FAM and HEX as discussed above:

| | | |
|---|---|---|
| FAM Channel | 0.94 | 0.06 |
| HEX Channel | 0.10 | 0.90 |
| | FAM | HEX |

For the crosstalk matrix above, readings made in the FAM channel will be a linear combination of FAM and HEX, where the weighting will be 94% FAM fluorescence and 6% HEX fluorescence. In theory, once the crosstalk matrix is known, it may be used to "unmix" or correct the raw data such that the FAM channel will be 100% FAM fluorescence and the HEX channel will be 100% HEX. However, this is generally not the case in practice.

One problem with crosstalk correction of PCR data according to the static crosstalk matrix method is that it often fails to some extent, and artifacts in one channel may be seen in another channel. It is typical to see both under-correction and over-correction, both of which lead to artifacts such as bumps or dips in PCR results or phantom melt peaks in melt curve data.

The failure of the static crosstalk matrix method may be attributable to several causes. For example, the elements of the crosstalk matrix may not be stable quantities in some embodiments, and they may vary somewhat between different runs of data (or even within a single run of data). It may be that conditions within each run of an assay sometimes operate to change the photophysical properties of the fluorescent species such that the correct crosstalk matrix values differ from test to test.

The matrix may also be temperature-dependent, and although fluorescent measurements during PCR are typically taken at the same temperature during each cycle, such temperature dependence may be a factor in other embodiments. For example, analyses of DNA melting temperatures may necessarily involve temperature variations during the assay. According to some embodiments, the static crosstalk method may include variations to take into account the temperature dependence of the elements of the crosstalk matrix. Such a temperature-dependent (but otherwise static) crosstalk matrix will also be treated herein as a variant of the static crosstalk matrix method. This disclosure, however, provides for dynamic adjustment of the crosstalk correction via analysis of the captured data.

Figure 6:
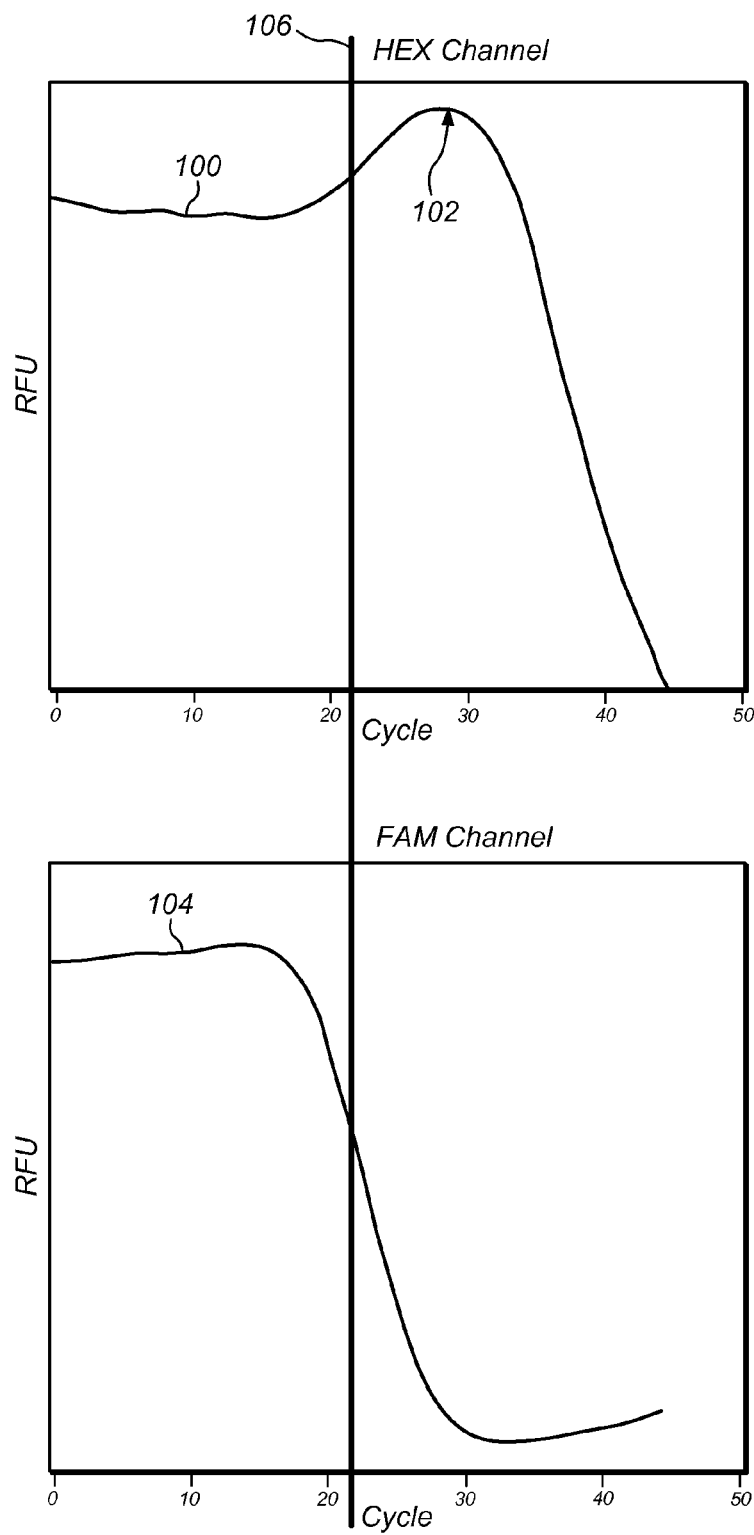
FIG. 6 shows an embodiment of a current crosstalk reduction system.

As noted above, failures to correct for crosstalk in the static crosstalk matrix method may typically come in one of two varieties: under-correction and over-correction. Turning now to FIG. 6, one example of data including over-correction of crosstalk is presented. The top graph of FIG. 6 shows HEX channel intensity 100 (in relative fluorescence units) processed according to the static crosstalk matrix method as a function of cycle number. The bottom graph shows the corresponding FAM channel intensity 104 (also processed according to the static crosstalk matrix method). Line 106 points out a correspondence between the two graphs at approximately cycle 22. As can be seen, a sharp decrease in the FAM channel occurs in the vicinity of line 106. Ordinarily, one would not expect such a change to coincide with a large change in the HEX channel. As shown, however, HEX channel intensity 100 exhibits an anomalous increase at artifact 102.

Artifact 102 may be explained as a consequence of over-correction of crosstalk. When the FAM channel experiences a large drop in signal, the system also observes a drop in the raw data for the HEX channel, because there is some amount of coupling between the two channels. Ideally, the system would interpret that drop in the HEX channel as entirely coming from the change in the FAM channel, and it would be exactly canceled by the crosstalk reduction technique described above. Thus ideally, even though the raw HEX channel data decreases, the system would determine via crosstalk correction that the actual corrected HEX channel data is essentially flat at that point.

In the example shown in FIG. 6, however, the crosstalk is over-corrected. In terms of the static crosstalk matrix technique described above, the coefficients of the crosstalk matrix corresponding to coupling between the FAM channel and the HEX channel are larger than they should be, which causes the system to treat the coupling as larger than it is in fact. Accordingly, when the raw FAM channel experiences a drop (and thus the raw HEX channel also shows a crosstalk-induced drop), the crosstalk correction increases the HEX channel by too much—the cancellation of the crosstalk effect is inexact, and the error is over-corrected. It is to be understood that the opposite problem may also occur in some instances. That is, if the values of the crosstalk matrix are smaller than they should be, then a drop in one channel can cause an anomalous drop in another channel instead of an anomalous rise.

Accordingly, it may be advantageous to adjust the values of the crosstalk matrix dynamically to attempt to obtain a more exact cancellation of crosstalk effects. In some embodiments, this may be accomplished by observing that a change in one signal should generally not correlate to changes in the other signals. Crosstalk may be viewed as properly corrected when large changes in one signal do not have a noticeable effect on other signals. In some embodiments, crosstalk correction may be applied between nearest-neighbor fluorescent species ("nearest" being defined in terms of absorption spectra, emission spectra, or both). In other embodiments, crosstalk correction may be applied across all fluorescent species, or across any subset thereof.

In some embodiments, it may be advantageous to define a suitable "crosstalk metric" for describing the degree to which changes in one channel are improperly reflected in another channel. Various ways of defining such a crosstalk metric are contemplated as being within the scope of this disclosure, and any of these may be advantageously used in various situations.

It may be observed that a large change in a signal from a particular channel corresponds to a large (either positive or negative) value for the time derivative of that signal. Thus it may be advantageous when defining the crosstalk metric to assign particular weight to situations where a large value in the time derivative for one signal corresponds to a large value in the time derivative for a different signal.

Accordingly, in one embodiment, the crosstalk metric may be defined in terms of the time derivatives of the signals from the respective channels. In some embodiments, the time derivative of the signal after it has already been corrected via the static crosstalk matrix method may be used; in other embodiments, the time derivative of the raw signal may be used. For purposes of this disclosure, the term "time derivative" may be defined as including any of several embodiments: continuous derivatives, discrete derivatives, finite differences, derivatives with respect to time, and derivatives with respect to cycle number.

In particular, the crosstalk metric may be defined in various embodiments in terms of a correlation between the time derivatives of the respective signals. For purposes of this disclosure, the term "correlation" may be defined as including any of several embodiments: continuous correlations, discrete correlations, pointwise products, cross-correlations, zero-shift cross-correlations, and convolutions.

According to embodiments of this disclosure, it may be advantageous to define such a crosstalk metric and then attempt to reduce or minimize its value. (For alternate definitions of the crosstalk metric, it is to be understood that increasing or maximizing may be the appropriate choice instead of reducing or minimizing)

For example, such a procedure may be carried out in some embodiments by treating the static crosstalk matrix for the device as a set of initial values. The value of the crosstalk metric may then be reduced or minimized by adjusting (e.g., iteratively adjusting) the values of this initial crosstalk matrix to achieve a reduction in the crosstalk metric.

In some embodiments, it may be advantageous to restrict the amount of adjustments allowed to the matrix coefficients. If no restrictions are in place, then simply attempting to minimize the crosstalk metric may result in unphysical calculations. For example, in some cases, if no restrictions are in place, negative coefficients may result in the "optimal" value of the crosstalk metric. Typically, however, such solutions may not be useful in the real world.

Accordingly, various types of restrictions may be implemented in some embodiments. For example, in various embodiments, the allowed values for the matrix coefficients may be restricted to be within 1%, 2%, 3%, 4%, 5%, 10%, 15%, 20%, 30%, 40%, or 50%, or any range derivable therein, of their initial values. Other types of restrictions may also be implemented, such as restricting all coefficients to positive (or alternatively, nonnegative) numbers.

Further, still other types of restrictions may be implemented as well. For example, in some embodiments it may be advantageous for the largest contribution in the corrected data to be from the original raw channel for that data. That is, at least in certain cases, it would not make physical sense for crosstalk contributions to account for more of a signal than the main component of the signal. One of ordinary skill in the art will understand that various other types of restrictions on the available adjustments to the values of the crosstalk matrix may be advantageous in some embodiments.

Figure 7B:
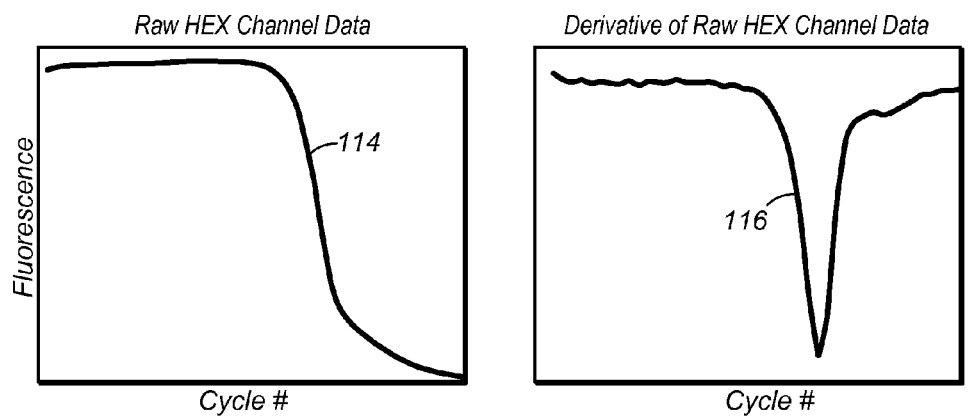
Figure 7C:
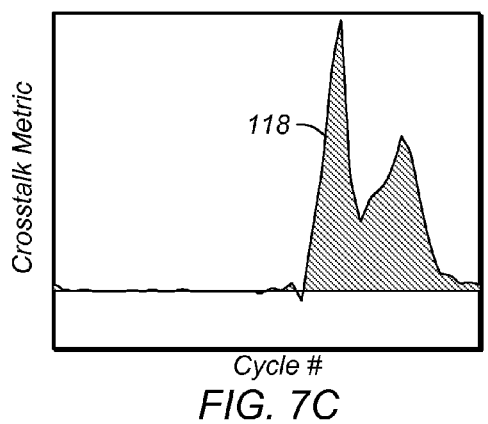
FIG. 7C shows a crosstalk metric for the data of FIGS. 7A and 7B.

Turning now to FIGS. 7A-7C, one embodiment of a crosstalk metric for describing crosstalk is shown. As above, this example refers to a PCR embodiment with a FAM channel and a HEX channel. FIG. 7A shows a raw fluorescence signal 110 as a function of cycle number for the FAM channel, as well as the corresponding time derivative 112. FIG. 7B shows the analogous data for the HEX channel, with raw fluorescence signal 114 and time derivative 116.

FIG. 7C shows a crosstalk metric according to one embodiment for the data of FIGS. 7A and 7B. In particular, graph 118 shows the pointwise product of time derivative 112 and time derivative 116. As noted above, such a pointwise product is a type of correlation between the two signals and is expected to display a large (either positive or negative) value when a large value in one derivative corresponds to a large value in the other. The crosstalk metric may be defined in this embodiment as the integral of the absolute value of graph 118. In other embodiments, various other ways of defining the crosstalk metric are contemplated. For example, the crosstalk metric may be defined as the integral of the square of the values of graph 118, the RMS average of the values of graph 118, the peak value of graph 118, the sum of values of graph 118, the sum of absolute values of graph 118, or any other suitable method.

Figure 8A:
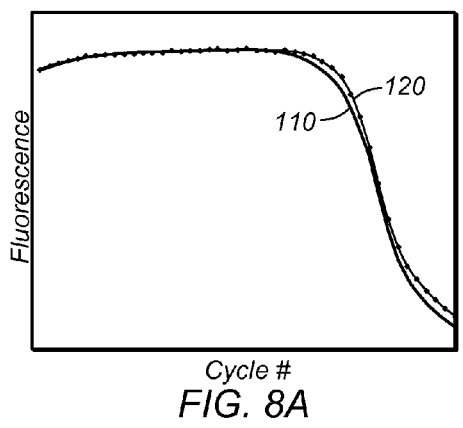
FIG. 8A shows an embodiment of the data of FIG. 7A with partial crosstalk correction.

Turning now to FIG. 8A, an example of partially corrected FAM channel data according to the static crosstalk matrix method is shown. Raw fluorescence signal 110 from FIG. 7A is shown again, along with partially corrected signal 120. For the sake of brevity, only the FAM channel data is shown in this example. The corresponding raw HEX channel data is typically also partially corrected according to the static crosstalk matrix method, however. The corresponding HEX channel data would typically be expected to show a similar, somewhat modest, improvement.

Figure 8B:
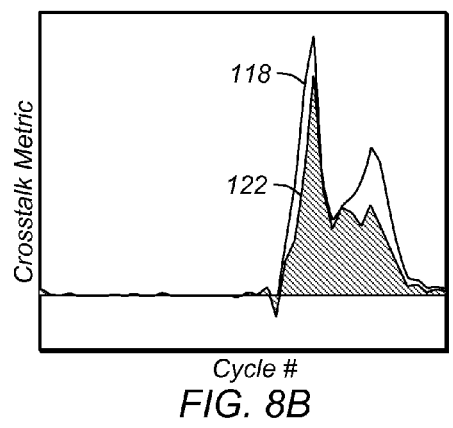
FIG. 8B shows a crosstalk metric for the data of FIG. 8A.

These somewhat modest improvements are reflected in FIG. 8B, which illustrates how partially corrected signal 120 from the FAM channel and the corresponding partially corrected signal from the HEX channel (not shown) affect the crosstalk metric (as defined above for purposes of this example). As can be seen, graph 122 is generally somewhat smaller than graph 118. The static crosstalk matrix method thus does provide some improvement in the crosstalk metric compared to the raw data, as is to be expected.

Figure 9A:
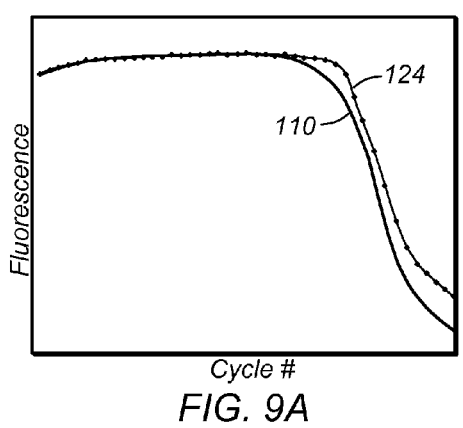
FIG. 9A shows an embodiment of the data of FIG. 7A with crosstalk correction according to this disclosure.

Turning now to FIG. 9A, an example of corrected FAM channel data according to an embodiment of this disclosure is shown. The final corrected signal 124 is shown in comparison to raw fluorescence signal 110. Here, too, the corresponding HEX channel data is omitted for brevity, but it may typically show similar improvements. In this embodiment, the corrected data is determined by first obtaining the partially corrected data of FIG. 8A according to the static crosstalk matrix method. The values of the static crosstalk matrix may be taken as initial values, which are then iteratively adjusted (in some embodiments, adjusted within certain restrictions as described above). As the values of the matrix elements are adjusted, the resulting corrected fluorescence signals and their respective derivatives also change, and the value of the crosstalk metric changes accordingly. Various known optimizations methods may be used in order to explore the parameter space of values for the matrix elements and determine the optimal values for the matrix elements to reduce or minimize the crosstalk metric (subject to the desired restrictions). For example, the Levenberg-Marquardt algorithm may be used in some embodiments. Various other optimization algorithms may also be used in various embodiments.

When the parameter space has been explored and the optimal values have been determined, the resulting crosstalk-corrected signal 124 may be output. The optimal crosstalk matrix may typically have a similar effect on the HEX channel data, which again is omitted for brevity.

Figure 9B:
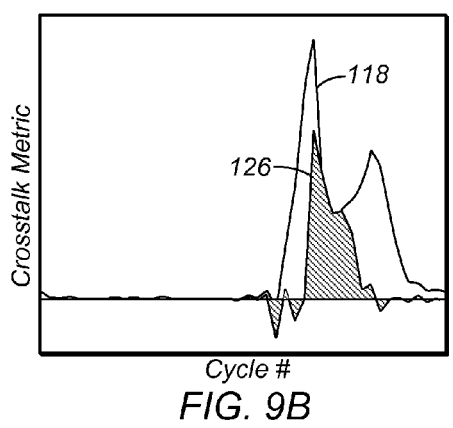
FIG. 9B shows a crosstalk metric for the data of FIG. 9A.

The improvements to this example provided by the present disclosure are reflected in FIG. 9B, which illustrates how corrected signal 124 from the FAM channel and the corresponding corrected signal from the HEX channel (not shown) affect the crosstalk metric. As can be seen, the area under the curve (representative of the crosstalk metric) of graph 126 is significantly smaller than in graph 118. The method of this disclosure accordingly may provide in some embodiments a very significant improvement over known methods.

As noted above, for the sake of simplicity and ease of exposition, some of this disclosure refers to crosstalk between two signals. One of ordinary skill in the art, however, will understand that the techniques herein generalize to more than two signals.

For example, in one embodiment, it may be desired to determine the crosstalk in a six-channel PCR device.

$$\begin{bmatrix} F_{chan1} \\ F_{chan2} \\ F_{chan3} \\ F_{chan4} \\ F_{chan5} \\ F_{chan6} \end{bmatrix} = \begin{pmatrix} M_{1,1} M_{1,2} M_{1,3} M_{1,4} M_{1,5} M_{1,6} \\ M_{2,1} M_{2,2} M_{2,3} M_{2,4} M_{2,5} M_{2,6} \\ M_{3,1} M_{3,2} M_{3,3} M_{3,4} M_{3,5} M_{3,6} \\ M_{4,1} M_{4,2} M_{4,3} M_{4,4} M_{4,5} M_{4,6} \\ M_{5,1} M_{5,2} M_{5,3} M_{5,4} M_{5,5} M_{5,6} \\ M_{6,1} M_{6,2} M_{6,3} M_{6,4} M_{6,5} M_{6,6} \end{pmatrix} \begin{bmatrix} C_{dye1} \\ C_{dye2} \\ C_{dye3} \\ C_{dye4} \\ C_{dye5} \\ C_{dye6} \end{bmatrix}$$

Various ways of determining the correlation between the respective derivatives of the six fluorescence signals are contemplated as being within the scope of this disclosure. One example includes simply multiplying all of the derivatives together (e.g., calculating the pointwise product of all six of the time derivatives). The crosstalk metric may then be calculated in the same way as in the two-signal embodiment, by (for example) calculating the integral of the absolute value of the pointwise product.

Another example includes determining the correlation between each pair of derivatives, and calculating the crosstalk metric based on these pairwise correlations. This technique may be straightforwardly generalized to determining the correlation between each triplet of derivatives, or each n-element set of derivatives. In some embodiments, it may be advantageous to take into account only the nearest neighbor(s). For example, it may be observed in some cases that signals do not exhibit significant crosstalk with signals more than one or two channels away. In those embodiments, it may then be advantageous to simply ignore such non-contributing signals in calculating the crosstalk metric. For instance, in an embodiment where data from a six-channel PCR device is corrected by only considering the crosstalk between a channel and its two immediate neighbors, the crosstalk metric may use triplets of derivatives. Four unique channel triplets would be defined in this scenario.

$$\begin{bmatrix} F_{chan1} \\ F_{chan2} \\ F_{chan3} \end{bmatrix} = \begin{pmatrix} M_{1,1} M_{1,2} M_{1,3} \\ M_{2,1} M_{2,2} M_{2,3} \\ M_{3,1} M_{3,2} M_{3,3} \end{pmatrix} \begin{bmatrix} C_{dye1} \\ C_{dye2} \\ C_{dye3} \end{bmatrix}$$

$$\begin{bmatrix} F_{chan2} \\ F_{chan3} \\ F_{chan4} \end{bmatrix} = \begin{pmatrix} M_{2,2} M_{2,3} M_{2,4} \\ M_{3,2} M_{3,3} M_{3,4} \\ M_{4,2} M_{4,3} M_{4,4} \end{pmatrix} \begin{bmatrix} C_{dye2} \\ C_{dye3} \\ C_{dye4} \end{bmatrix}$$

$$\begin{bmatrix} F_{chan3} \\ F_{chan4} \\ F_{chan5} \end{bmatrix} = \begin{pmatrix} M_{3,3} M_{3,4} M_{3,5} \\ M_{4,3} M_{4,4} M_{4,5} \\ M_{5,3} M_{5,4} M_{5,5} \end{pmatrix} \begin{bmatrix} C_{dye3} \\ C_{dye4} \\ C_{dye5} \end{bmatrix}$$

$$\begin{bmatrix} F_{chan4} \\ F_{chan5} \\ F_{chan6} \end{bmatrix} = \begin{pmatrix} M_{4,4} M_{4,5} M_{4,6} \\ M_{5,4} M_{5,5} M_{5,6} \\ M_{6,4} M_{6,5} M_{6,6} \end{pmatrix} \begin{bmatrix} C_{dye4} \\ C_{dye5} \\ C_{dye6} \end{bmatrix}$$

The crosstalk minimization method described above may be implemented independently to find the optimal correction matrix for each of the four triplets such that all channels were corrected. The corrected data vector associated with dyes one and two may be determined by finding the optimal correction matrix from the first data triplet. The corrected data vectors associated with dyes three and four would be determined from the second and third triplets respectively. The corrected data vector associated with dyes five and six would be determined by finding the optimal correction matrix from the last data triplet.

In another embodiment the crosstalk observed in fluorescence measurements between wells of a multi-well plate can be corrected using this algorithm. In this embodiment one may in some embodiments consider fluorescence measurements from individual wells to be linear combinations of fluorescence from the desired well and fluorescence from neighboring wells inadvertently detected simultaneously.

$$\begin{bmatrix} F_{chan1\_well1} \\ F_{chan1\_well2} \\ F_{chan1\_well3} \end{bmatrix} = \begin{pmatrix} M_{1,1} M_{1,2} M_{1,3} \\ M_{2,1} M_{2,2} M_{2,3} \\ M_{3,1} M_{3,2} M_{3,3} \end{pmatrix} \begin{bmatrix} C_{well1} \\ C_{well2} \\ C_{well3} \end{bmatrix}$$

In this scenario one would attempt to minimize the correlation (as described above) in a given spectral channel between wells.

In yet another embodiment, crosstalk peaks observed in multiplexed capillary electrophoresis can be corrected by similarly defining the time varying signals from each capillary of a multiplexed capillary electrophoresis device as linear combinations of the intended capillary and its spatial neighbors. The crosstalk between capillaries can similarly be minimized by iteratively adjusting the linear combination matrix so as to minimize a measure of the correlation between channels. The method of calculating a crosstalk metric described above is a suitable determiner of the correlation between capillary channels.

Figure 10:
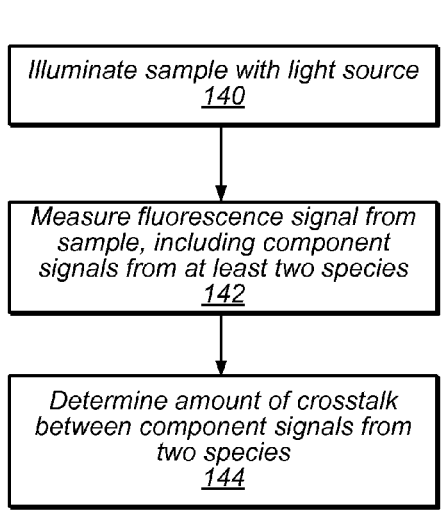
FIGS. 10-11 show exemplary process flows in accordance with this disclosure.

Turning now to FIG. 10, an exemplary process flow according to one embodiment of this disclosure is presented.

Flow begins at block 140. At block 140, a sample is illuminated with a light source. The sample may be any of a variety of samples, and includes a plurality of fluorescent species. In various embodiments, the fluorescent species may be different types of fluorophores, the same types of fluorophores within different wells, etc. In this example, at least two of the fluorescent species are excited by the illumination. Flow proceeds to block 142.

At block 142, a fluorescence signal is measured from the sample. In this embodiment, the fluorescence signal includes signals from the at least two fluorescent species that have been excited by the illumination. Flow proceeds to block 144.

At block 144, the amount of crosstalk between the signals from the two fluorescent species is determined. This determining may be carried out, for example, by an assaying device. In this embodiment, the determination of the amount of crosstalk is based on a correlation respective time derivatives of the signals from the two fluorescent species. This may be accomplished, in one embodiment, by examining a pointwise product of the respective time derivatives. For example, a crosstalk metric may be defined as an integral of this pointwise product (e.g., an integral of the absolute value of this pointwise product). Flow ends at block 144.

Figure 11:
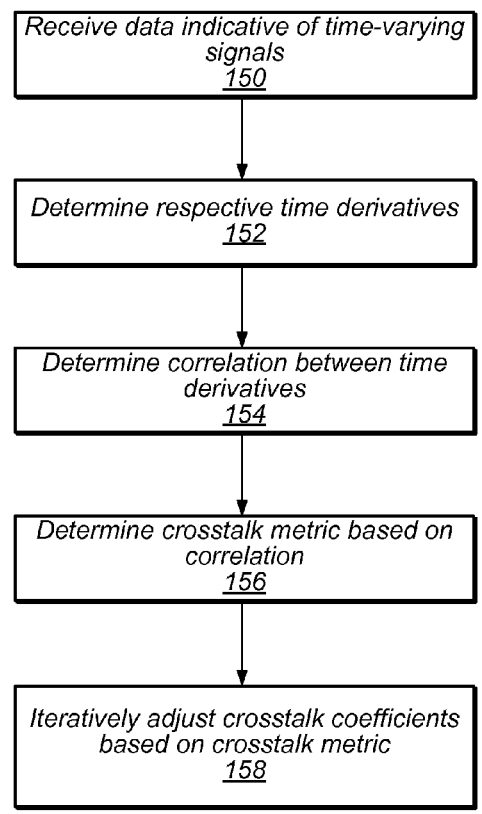

Turning now to FIG. 11, another exemplary process flow according to an embodiment of this disclosure is presented.

Flow begins at block 150. At block 150, a computing device receives data indicative of a plurality of time-varying signals. In this example, the signals include crosstalk between at least a first and a second one of the signals. Flow proceeds to block 152.

At block 152, the computing device determines respective time derivatives of the signals based on the received data. For example, the time derivatives may include discrete or continuous derivatives, and they may include differentiation with respect to any suitable variable (e.g., time or cycle number as appropriate). Flow proceeds to block 154.

At block 154, the computing device determines a correlation between the time derivatives. For example, this may include a cross-correlation, a convolution, and-or a pointwise product between the derivatives. Any suitable method of determining a correlation is acceptable. Flow proceeds to block 156.

At block 156, the computing device determines a crosstalk metric based on the correlation. For example, the crosstalk metric may be an integral of the correlation between the derivatives, such as an integral of the absolute value of the pointwise product between the derivatives. Flow proceeds to block 158.

At block 158, a plurality of crosstalk coefficients are iteratively adjusted based on the crosstalk metric. For example, the coefficients may be adjusted in order to minimize the crosstalk metric. In other definitions of the crosstalk metric, it may be suitable to maximize the crosstalk metric. In some embodiments, the computing device may attempt to reduce (or increase) the crosstalk metric subject to a set of restrictions, such as ensuring that all coefficients remain positive. Other such restrictions have been discussed above, and variations will be apparent to one of ordinary skill in the art. Flow ends at block 158.

Figure 12:
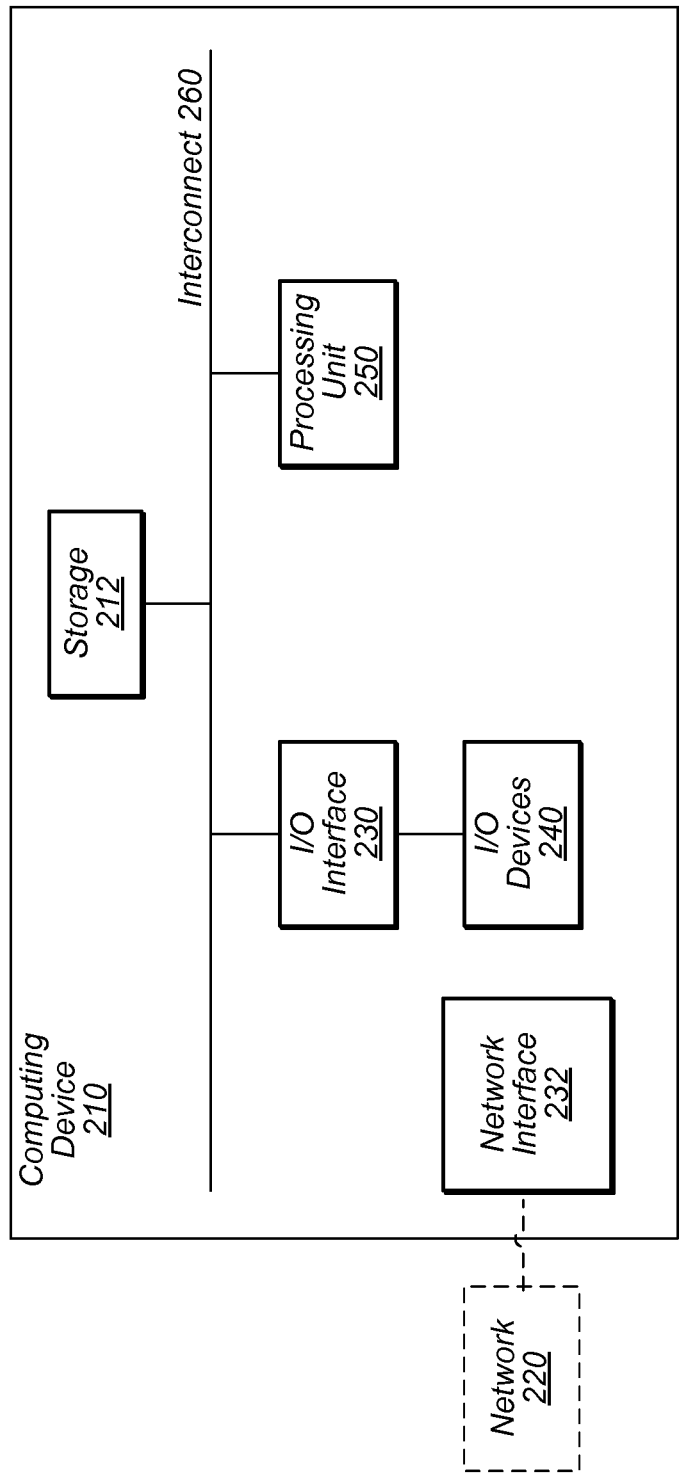
FIG. 12 shows a block diagram of one embodiment of a system usable to implement various portions of this disclosure.

Turning now to FIG. 12, a block diagram of one embodiment of computing device 210 is depicted. Computing device 210 may be used to implement various portions of this disclosure. Computing device 210 may be any suitable type of device, including, but not limited to, a personal computer system, desktop computer, laptop or notebook computer, mainframe computer system, web server, workstation, or network computer. As shown, computing device 210 includes processing unit 250, storage 212, input/output (I/O) interface 230 coupled via an interconnect 260 (e.g., a system bus). I/O interface 230 may be coupled to one or more I/O devices 240. Computing device 210 further includes network interface 232, which may be coupled to network 220 for communications with, for example, other computing device.

As described above, processing unit 250 includes one or more processors. In some embodiments, processing unit 250 includes one or more coprocessor units. In some embodiments, multiple instances of processing unit 250 may be coupled to interconnect 260. Processing unit 250 (or each processor within 250) may contain a cache or other form of on-board memory. In some embodiments, processing unit 250 may be implemented as a general-purpose processing unit, and in other embodiments it may be implemented as a special purpose processing unit (e.g., an ASIC). In general, computing system 210 is not limited to any particular type of processing unit or processor subsystem.

As used herein, the term "processing unit" refers to circuitry configured to perform operations or to a memory having program instructions stored therein that are executable by one or more processors to perform operations. Accordingly, a processing unit may be implemented as a hardware circuit implemented in a variety of ways. The hardware circuit may include, for example, custom very-large-scale integration (VLSI) circuits or gate arrays, off-the-shelf semiconductors such as logic chips, transistors, or other discrete components. A processing unit may also be implemented in programmable hardware devices such as field programmable gate arrays, programmable array logic, programmable logic devices, or the like. A processing unit may also be configured to execute program instructions from any suitable form of non-transitory computer-readable media to perform specified operations.

Storage subsystem 212 is usable by processing unit 250 (e.g., to store instructions executable by and data used by processing unit 250). Storage subsystem 220 may be implemented by any suitable type of physical memory media, including hard disk storage, floppy disk storage, removable disk storage, flash memory, random access memory (RAM-SRAM, EDO RAM, SDRAM, DDR SDRAM, RDRAM, etc.), ROM (PROM, EEPROM, etc.), and so on. Storage subsystem 212 may consist solely of volatile memory in one embodiment. Storage subsystem 212 may store program instructions executable by computing device 210 using processing unit 250, including program instructions executable to cause computing device 210 to implement the various techniques disclosed herein.

I/O interface 230 may represent one or more interfaces and may be any of various types of interfaces configured to couple to and communicate with other devices, according to various embodiments. In one embodiment, I/O interface 230 is a bridge chip from a front-side to one or more back-side buses. I/O interface 230 may be coupled to one or more I/O devices 240 via one or more corresponding buses or other interfaces. Examples of I/O devices include storage devices (hard disk, optical drive, removable flash drive, storage array, SAN, or an associated controller), network interface devices, user interface devices or other devices (e.g., graphics, sound, etc.).

Various articles of manufacture that store instructions (and, optionally, data) executable by a computing system to implement techniques disclosed herein are also contemplated. These articles of manufacture include non-transitory computer-readable memory media. The contemplated non-transitory computer-readable memory media include portions of a memory subsystem of a computing device as well as storage media or memory media such as magnetic media (e.g., disk) or optical media (e.g., CD, DVD, and related technologies, etc.). The non-transitory computer-readable media may be either volatile or nonvolatile memory.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A method, comprising:
    illuminating a sample with a light source, wherein the sample includes a plurality of fluorescent species, and wherein illuminating the sample with the light source excites at least two of the plurality of fluorescent species;
    measuring at least two fluorescence signals from the sample, wherein the at least two fluorescence signals include component signals from the at least two of the plurality of fluorescent species; and
    determining, by an assaying device, an amount of crosstalk between the at least two fluorescence signals, wherein the determined amount of crosstalk is based on a correlation between respective time derivatives of the at least two fluorescence signals.

2. The method of claim 1, wherein determining the amount of crosstalk includes:
    estimating the amount of crosstalk based on an initial crosstalk matrix; and
    determining an adjusted crosstalk matrix by adjusting elements of the initial crosstalk matrix based on the correlation between the respective time derivatives of the at least two fluorescence signals.

3. The method of claim 2, wherein adjusting the elements includes iteratively adjusting the elements within defined ranges of corresponding values from the initial crosstalk matrix.

4. The method of claim 1, wherein the correlation between the respective time derivatives of the at least two fluorescence signals is based on a pointwise product of the respective time derivatives.

5. The method of claim 1, wherein an optimal crosstalk correction is determined by minimizing the correlation between the respective time derivatives of the at least two fluorescence signals.

6. The method of claim 1, further comprising outputting crosstalk-corrected fluorescence signals for the at least two of the plurality of fluorescent species.

7. The method of claim 1, wherein the sample is a multi-well sample.

8. The method of claim 7, wherein the at least two of the plurality of fluorescent species are disposed within corresponding at least two wells of the multi-well sample.

9. The method of claim 8, wherein the at least two of the plurality of fluorescent species are a single type of fluorescent species.

10. An apparatus, comprising:
a light source configured to illuminate a sample including at least first and second fluorescent species;
a detector configured to receive fluorescent light from the first and second fluorescent species in response to the illumination; and
a processing unit configured to:
receive first data indicative of the received fluorescent light from the first fluorescent species and second data indicative of the received fluorescent light from the second fluorescent species; and
determine an amount of crosstalk between the first and second data, wherein the determined amount of crosstalk is based on a correlation between respective time derivatives of the first and second data.

11. The apparatus of claim 10, wherein the sample includes at least six fluorescent species.

12. The apparatus of claim 10, wherein the sample includes exactly two fluorescent species.

13. The apparatus of claim 10, wherein the light source is a broad-spectrum light source, and wherein the apparatus further includes a filter operable to restrict the illumination to a specified wavelength band.

14. The apparatus of claim 10, wherein the light source is a narrow-spectrum light source.

15. The apparatus of claim 10, wherein the sample is a single-tube PCR sample.

16. The apparatus of claim 10, wherein the sample is a multi-well PCR sample.

17. The apparatus of claim 16, wherein the first fluorescent species is disposed within a first well of the multi-well PCR sample, and wherein the second fluorescent species is disposed within a second well of the multi-well PCR sample.

18. The apparatus of claim 17, wherein the first fluorescent species and the second fluorescent species are a single type of fluorescent species.

19. A non-transitory computer-readable medium having instructions coded thereon that, when executed by a computing device, cause the computing device to carry out operations comprising:
receiving data indicative of a plurality of time-varying signals, wherein the signals include crosstalk between at least first and second ones of the signals;
determining respective time derivatives for the signals based on the data;
determining an amount of correlation between the respective time derivatives;
determining a crosstalk metric indicative of a level of crosstalk for the signals, wherein the crosstalk metric is based on the amount of correlation; and
iteratively adjusting a plurality of crosstalk coefficients indicative of the crosstalk between the signals, wherein the adjusting is based on the crosstalk metric.

20. The medium of claim 19, wherein iteratively adjusting the plurality of crosstalk coefficients includes adjusting the crosstalk coefficients subject to a set of restrictions.

21. The medium of claim 20, wherein the set of restrictions includes preventing negative values for the crosstalk coefficients.

22. The medium of claim 19, wherein the amount of correlation is a pointwise product of the respective time derivatives.

23. The medium of claim 19, wherein the crosstalk metric is based on an integral of the amount of correlation.

* * * * *